(12) United States Patent
Paul et al.

(10) Patent No.: US 7,055,377 B2
(45) Date of Patent: Jun. 6, 2006

(54) QUARTZ CRYSTAL SENSOR CELL

(75) Inventors: Frank Paul, Harlow (GB); Karl Pavey, Newport (AU); Richard C Payne, The Frythe (GB)

(73) Assignee: Akubio Limited, Cambridge (GB)

( * ) Notice: Subject to any disclaimer, the term of this patent is extended or adjusted under 35 U.S.C. 154(b) by 47 days.

(21) Appl. No.: 10/344,022

(22) PCT Filed: Aug. 2, 2001

(86) PCT No.: PCT/EP01/08922

§ 371 (c)(1),
(2), (4) Date: Aug. 28, 2003

(87) PCT Pub. No.: WO02/12873

PCT Pub. Date: Feb. 14, 2002

(65) Prior Publication Data

US 2004/0016297 A1    Jan. 29, 2004

(30) Foreign Application Priority Data

Aug. 8, 2000 (GB) .................. 0019336.7
Aug. 8, 2000 (GB) .................. 0019340.9

(51) Int. Cl.
*G01N 11/10* (2006.01)
*H01L 41/04* (2006.01)
(52) U.S. Cl. .............. 73/54.41; 73/54.24; 310/344
(58) Field of Classification Search .......... 73/54.41, 73/54.24, 54.25; 310/344
See application file for complete search history.

(56) References Cited

U.S. PATENT DOCUMENTS

| 4,368,400 | A | | 1/1983 | Taniguchi et al. |
| 4,561,286 | A | * | 12/1985 | Sekler et al. ............ 73/24.06 |
| 5,021,701 | A | | 6/1991 | Takahashi et al. |
| 5,201,215 | A | | 4/1993 | Granstaff et al. |
| 5,455,475 | A | | 10/1995 | Josse et al. |
| 6,189,367 | B1 | * | 2/2001 | Smith et al. ............ 73/19.03 |
| 6,472,798 | B1 | | 10/2002 | Kishimoto |

FOREIGN PATENT DOCUMENTS

| DE | 44 04 309 A | 8/1995 |
| JP | 08 075629 | 7/1996 |
| JP | 09 304259 | 8/1998 |
| WO | WO 00/25118 | 5/2000 |

OTHER PUBLICATIONS

Komplin et al., "A High-Stability Quartz Crystal Microbalance Electrode for Simultaneous Solution-Phase Electrochemistry/Microgravitometry", Review of Scientific Instruments, American Institute of Physics, New York, vol. 64, NR 6, pp. 1530-1535.

* cited by examiner

*Primary Examiner*—Hezron Williams
*Assistant Examiner*—John Fitzgerald
(74) *Attorney, Agent, or Firm*—Howson & Howson

(57) ABSTRACT

A quartz crystal sensor cell in which the sensor is secured to the base of a well defining a test sample space by a layer of adhesive between the respective peripheral surfaces. Also a quartz crystal sensor cell is provided in which the quartz sensor crystal is inclined relative to the opposite surface of the test sample space. These constructions respectively improve distinctness of the "Q" peak and problems from reflected waves in the space.

19 Claims, 3 Drawing Sheets

QUARTZ CRYSTAL SENSOR CELL

This invention relates to improvements in cells for quartz crystal sensors.

The quartz crystal sensor is a mass sensing device with the ability to measure very small mass changes on the surface of a piezoelectric quartz crystal. A device using such a quartz crystal sensor is generally known in the art as a quartz crystal microbalance. The quartz crystal is mounted in a cell in which materials under test can be exposed to the surface of the crystal or on a receptor coated on the crystal surface. Quartz crystal sensors were originally developed to detect deposits on the crystal sensor under vacuum conditions. When the crystal is in a gaseous environment and is energised by an oscillator circuit there is a well-defined relationship between frequency shift and a mass deposited on the crystal surface. In liquid environments the density and viscosity of the liquid and visco-elastic properties of the receptor affect the response. Mass changes as small as the deposit of a single layer of atoms can be detected.

Further developments to measure deposits from liquid carriers flowing through the cell have needed to face problems caused by damping of the sensitivity of the sensor due to the liquid in contact with the crystal. This is addressed in our patent application PCT/EP99/08148 which proposes novel circuitry to drive the crystal.

In our continuing study of quartz crystal sensors, we have found that further problems in sensitivity and reproducibility of results arise from the physical configuration of existing cells. A typical configuration of a cell is shown in FIG. 1 of the accompanying drawings. In this cell, a sample space (1) is formed by clamping a quartz crystal (2) between upper and lower housing parts (4) and (3); for example by passing bolts through bore holes (5). The upper housing part (4) is formed with a cylindrical depression or "well" so that the sample space (1) is delimited by the upper surface of the quartz crystal (2), the sidewalls (6) of the depression and an upper surface (7) bridging the sidewalls. Inlet and outlet ports (8,9) formed in the upper housing part (4) allow a fluid carrying a sample to pass into and out of the sample space. Electrodes (10) and (11) on opposite surfaces of the quartz crystal (2) allow the crystal to be driven by an oscillator circuit.

Conventionally the quartz crystal (2) is secured between the upper and lower body parts (4) and (3) by resilient O-rings (12) and (13) which absorb some of the clamping pressure and seal the sample space. In practice, this arrangement results in poor reproducibility of repeated sampling because of variations from run to run in the torque applied in clamping the sensor in the cell. This can cause variations in crystal alignment and even cracking of the crystals. The variations in compression of the crystal and in alignment result in an indistinct peak "Q" value, the parameter by which the frequency change is measured.

We have found that this problem can be overcome by constructing a cell in which the crystal sensor is secured directly to the housing.

Accordingly in a first aspect the present invention provides a quartz crystal sensor cell comprising a housing having a well to receive a sample carrier fluid, an aperture in the base of the well to receive a quartz crystal sensor, and a quartz crystal sensor located in the base of the well so that a peripheral surface of the sensor lies against a peripheral surface of the aperture, and the sensor is secured to the base of the well by a layer of adhesive between the respective peripheral surfaces.

The base of the cell may consist of a peripheral flange directed inwardly from the side walls of the well to define a central aperture. Suitably, the well is formed as a cylindrical bore having an internal annular flange to form the apertured base of the well. The sensor is typically circular in shape and has a diameter greater than the diameter of the central aperture defined by the annular flange.

The sensor may be adhered to the flange by forming a continuous bead or layer of curable adhesive on the flange, and placing the sensor on the bead while the adhesive cures, to form an adhesive layer between the respective overlapping edges of the sensor and flange. Preferably, the curable bead of adhesive is a flowable composition and the sensor is allowed to settle on the bead under its own weight while the bead cures as a thin interlayer. Suitably the sensor is located on the underside of the flange relative to the void space of the well, requiring that the cell is inverted as the sensor is applied. Non-solvent-based adhesives are preferred to avoid problems with solvent removal. However, a solvent-based adhesive could be used to deposit a pressure sensitive adhesive layer.

The sensor may be secured non-compressively by any adhesive. However, use of a rigid-setting adhesive may itself impose stresses on the sensor. Therefore, the adhesive is preferably selected so as to cure to form a resilient interlayer between the sensor and the flange. Silicone polymers have been found to be especially suitable.

The cell may be closed by a housing part positioned across the mouth of the well. Preferably this closure has inlet and outlet ports enabling a fluid sample carrier to pass through the cell. In this configuration the cell can be used as a flow cell, to measure dynamic characteristics as a sample is deposited on the sensor. In particular, such cells may be used to investigate the binding characteristics between a sample in the carrier fluid and a substrate pre-deposited on the sensor.

It is not always necessary that a quartz crystal sensor cell is operated as a flow cell. In some situations, the analytical requirements are simply to detect a binding event between a substrate deposited on the sensor surface and a test material suspended or dissolved in the carrier liquid. In that case, it is not necessary for the closure part to be provided with inlet and outlet ports and connectors for attaching feed tubing. Instead, in an alternative embodiment, the closure may be provided with a single port, which may be simply a centrally located aperture or bore hole, through which a sample carrier liquid can be injected into the well to contact, preferably covering the sensor.

An array of such cells may be used with an automated sample injector system. In this configuration the sensor can be used simply to detect binding events when dynamic information is not necessary.

In a particular embodiment, multiple cells are formed as bore holes in a rectangular housing block, for example, in a standard 96 cell array that may be used with a conventional automated sample injector. Each well has a sensor adhered to a peripheral flange forming its base. In this embodiment, the wells may be fully open without any closure.

Our study of quartz crystal microbalance flow cells has also revealed that reflected waves occur between the crystal and the substantially parallel upper boundary surface of the sample space. We have discovered that this problem may be overcome by use of an asymmetric sample space.

Accordingly, in a second aspect the present invention provides a flow cell for a quartz crystal sensor comprising a housing, a quartz crystal mounted in the housing to form one boundary surface of a sample space delimited by the housing internal wall surfaces and an upper housing surface bridging the housing walls, and having inlet and outlet ports on the housing for conveying a sample carrier into and out of the sample space, characterised in that the upper housing surface is inclined to the plane of the quartz crystal.

This construction of flow cell of this second aspect of the invention may be used with flow cells of otherwise conventional construction, e.g. with their quartz crystal secured between a pair of upper and lower resilient O-rings. Preferably it is used with the flow cell of the above described first aspect of the invention with its sensor secured to the base of a well by a layer of adhesive.

By "inclined" we mean generally non-parallel. We have found that if the inclination of the upper boundary surface is too steep, bubbles tend to form in the sample space. Accordingly, the angle of inclination must be selected so as to balance the effect of minimising both the occurrence of reflected waves and the formation of bubbles within the sample space. We have found that an angle of inclination between 1–5° is suitable, preferably between 1–3°, about 2° (e.g. + or −0.5°) being effective.

Preferably the angle of inclination is such that the upper boundary surface rises relative to the crystal sensor, between the inlet and outlet ports. When the inlet and outlet ports are formed in the upper boundary surface, then preferably the outlet is at or near the highest point of the sample space i.e. where there is maximum separation between the upper housing surface and the crystal.

When intended for use as a flow cell, the cell housing is conveniently formed in two parts, a first (lower) housing part having a well with a central aperture in which the crystal sensor is secured to form a lower boundary surface of the sample space, and a second (upper) housing part which is located on the lower part over the well and crystal sensor to form an upper boundary surface of the sample space.

The well is suitably a hollow cylindrical void having an internal annular flange to form the base. The sensor is typically circular in shape and has a diameter greater than the diameter of the central aperture defined by the annular flange.

Typically when the upper housing part is clamped to the lower housing part it engages a resilient O-ring to seal the sample space. Suitably the O-ring is seated against a peripheral flange in the well and the sensor is adhered to the opposite side of the flange. This arrangement minimises the transfer of clamping forces to the crystal.

The inlet and outlet ports for the flow cell are most conveniently provided in the upper housing part, most suitably opening into the sample space at the upper boundary surface. It is preferred that the ports are oriented so that the sample carrier enters and leaves the sample space in a direction substantially normal to the surface of the quartz crystal, though for some practical situations alternative orientations may be preferred.

For easy assembly and maintenance it is advantageous that the sensor is mounted in a separate carrier block comprising the well and flange for seating the sensor. The carrier block is located in a base block to which the upper housing part is bolted as a closure for the well.

The present invention is described in more detail below with a reference to the accompanying drawings which show, by way of example only:

Figure 1:
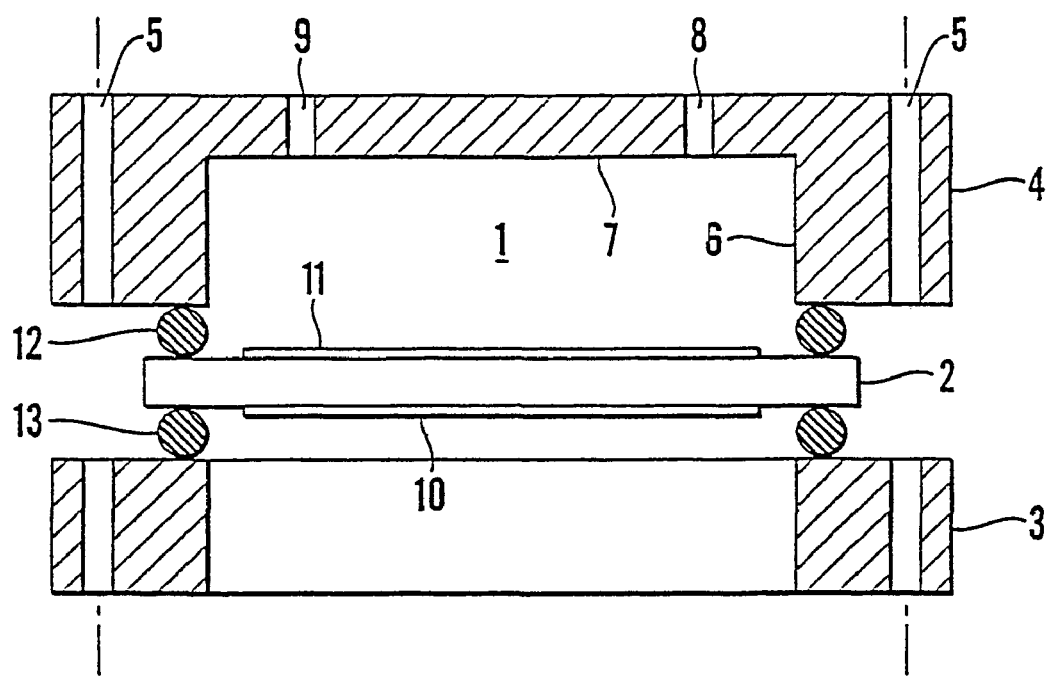
FIG. 1 is a schematic cross-section through a prior art flow cell.

FIG. 1 shows a prior art construction already described above. As mentioned previously, we have found that elements of this design are unsatisfactory from the point of view of reproducibility of results and distinctness of the "Q" value peak. These arise inter alia from the clamping of the crystal sensor between housing parts (3) and (4) via resilient O-rings (12) and (13).

Figure 2:
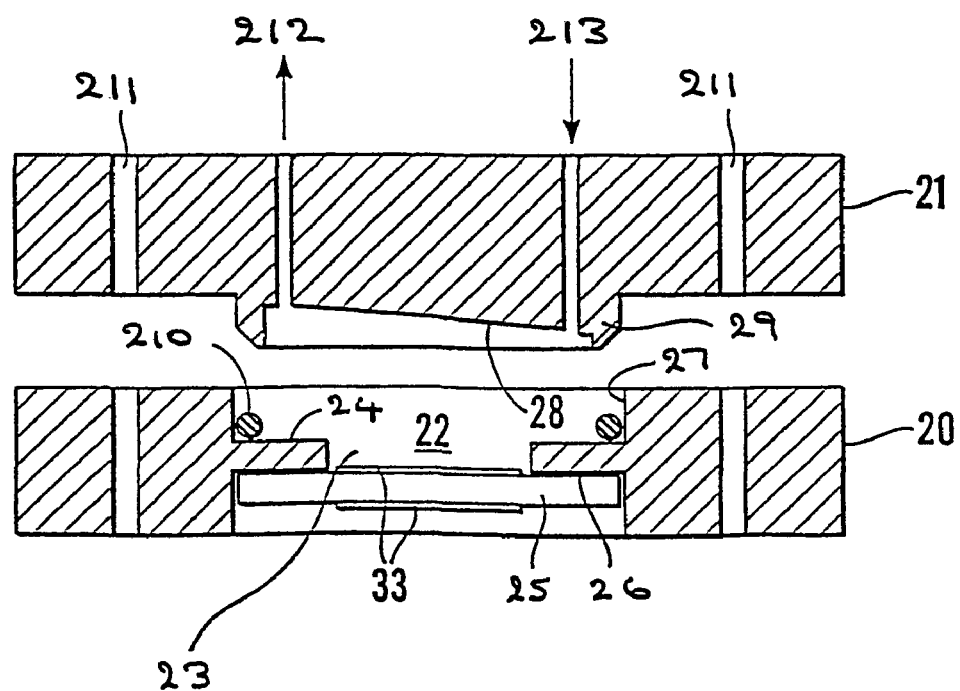
FIG. 2 is a schematic cross-section through a flow cell in accordance with both aspects of the present invention.

FIG. 2 shows (schematically and not to scale) a flow cell constructed in accordance with the findings of the present invention.

The cell has a two-part structure comprising a lower (base) body block (20) and an upper (closure) body block (21) which together form a housing. The lower body block (20) is formed to define a well (22), which is a cylindrical void having an aperture (23) in its base, and surrounded by a peripheral flange (24) which serves as a seat for a quartz crystal sensor (25). The quartz sensor (25), a thin wafer of quartz, is secured to the lower surface of the flange (24) by an adhesive layer (26). Suitably this is achieved by use of a curable silicone adhesive which cures in air to form a resilient layer. This allows the crystal (25) to be directly secured to the flange (24) without the risk of applying uneven or non-reproducible stresses to the crystal sensor. By inverting the lower block (20) and injecting a continuous bead of adhesive (26) against the flange (24), then allowing the sensor (25) to rest against the bead under the influence of gravity only, the layer of adhesive (26) attaches the sensor (25) to the flange (24) without imposing external stresses.

To enclose a sample space in the well (22), the upper body part (21) is located against the lower body part (20), effectively forming a closure to the well (22), so that a sample space is delimited by the side walls (27) of the well (22), the upper surface of the crystal (25) and the under surface (28) of the upper block (21).

In accordance with the present invention, this surface (28) is inclined so that it is not parallel with the crystal sensor (25) when the upper and lower body blocks (20), (21) are mated together. We have found that an angle of inclination of around 2° gives good results, providing a balance between the reduction of the effects of reflected waves, and the formation of bubbles which occur as the angle of inclination is increased.

To ensure sealing of the sample space in the well (22), the upper body block (21) is shaped to provide an annular projection (29) which protrudes into the well (22) to engage a resilient O-ring seal (210), which conveniently rests on the upper surface of the flange (24). The annular projection (29) surrounds the surface (28) of upper block (21) forming a recess which defines the upper part of the sample space in the well (22).

The two body parts (20, 21) may be secured to each other, compressing the O-ring seal (210), by bolts (not shown) passed through bolt holes (211) formed in the blocks (20, 21).

The upper body block (21) is also formed with bore holes (212) and (213) acting respectively as inlets and outlets for a liquid carrier which conveys test material into the sample space in the well (22). Preferably these bore holes (212, 213) are arranged so that the carrier enters and exists from the sample space in a direction substantially at right angles to the crystal sensor (25), although their orientation may need to be varied to suit the external connections to tubing by which the carrier liquid is fed and removed.

Electrodes (214) are positioned on each surface of the crystal sensor (25) so that the piezoelectric crystal can be driven by an external oscillator circuit. The electrodes may be connected to a conventional oscillator circuit, or more preferably an oscillator circuit as described in PCT/EP99/08148, by silver conductive paint leads (not shown) carried from the electrodes around the edges of the crystal to conductors inserted into the housing.

Figure 3:
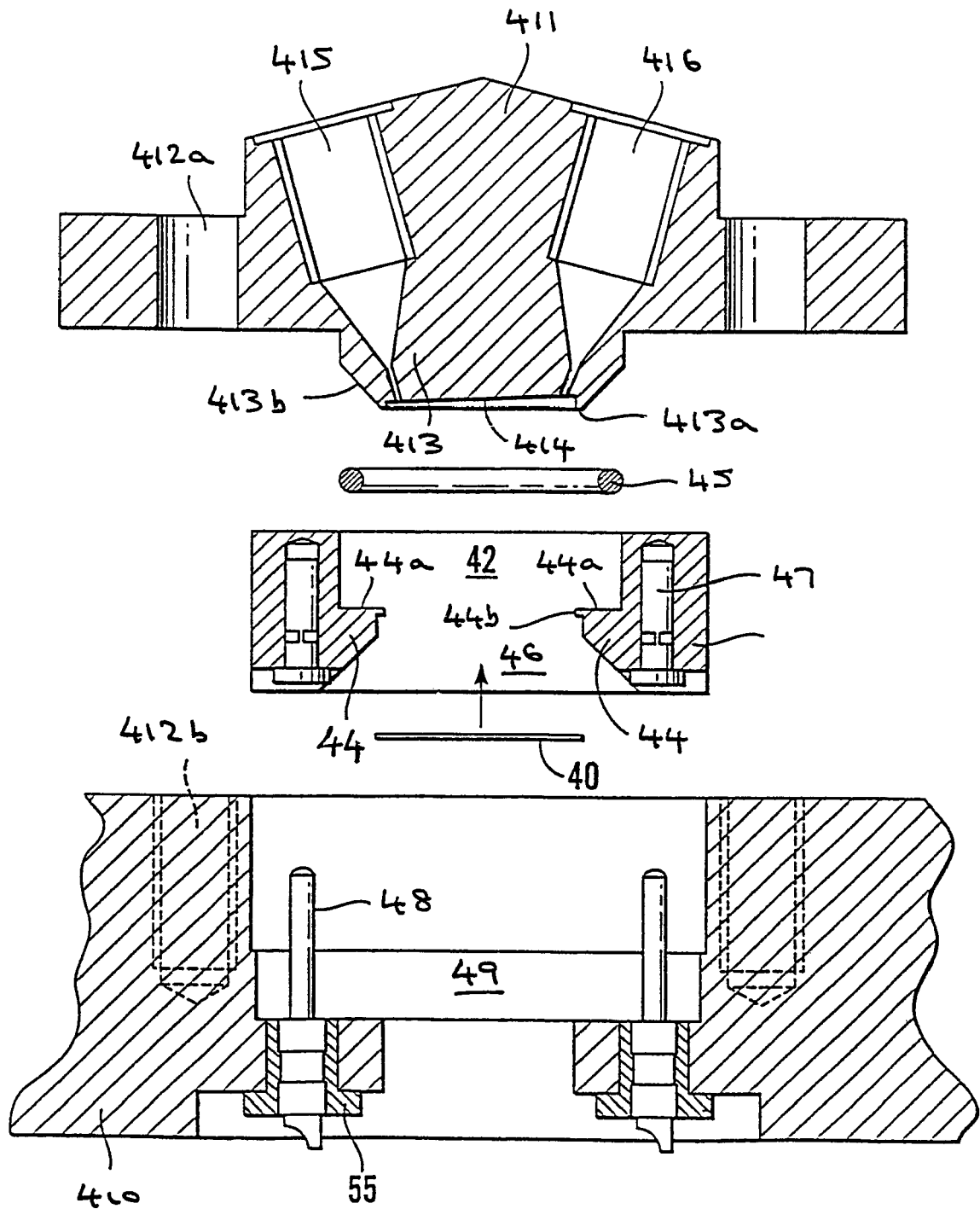
FIG. 3 is a cross-section through a practical embodiment of a flow cell in accordance with both aspects of the present invention.

Having described the principles of this invention with respect to the schematic embodiment of FIG. 2, we now refer to the practical embodiment shown in FIG. 3 of the accompanying drawings in which the above-described principles are implemented.

FIG. 3 shows a sectional view through a quartz crystal sensor flow cell. In this embodiment, quartz crystal sensor (40) is secured to a carrier block (41) which locates in a base block (48). The combined carrier (41) and base block (48) are equivalent to the lower housing part (20) of FIG. 2. In an analogous manner to the FIG. 2 embodiment, the carrier block (41) comprises a cylindrical well (42) and a circular aperture (43) in its base, and being surrounded by a peripheral flange (44). The flange (44) has two portions: a relatively thick root portion (44a), adjacent the walls of well (42) which supports an O-ring (45); and a relatively thin extension (44b) which provides a flange surface to receive the sensor (40). As in FIG. 2, the sensor (40) is adhered to the underside (relative to the sample space of the well) of the flange (44b), sitting in a reversed well (46) defined by the edges of the flange root (44a).

Conductive sockets (47) are positioned in bores in the housing of the carrier (41) and the sockets (47) are connected by conducting leads to the electrodes of the sensor (40), when the latter is adhered to the flange (44b). The sensor carrier block (41) is located, via the conductive sockets (47), on conductor pins (48) protruding into a well (49) formed in the base block (410). The conductor pins (48) are in turn connected to the oscillator circuit (not shown) which drives the crystal sensor (40).

A closure part (411) bolts on to the base (410) through bolt holes (412b, 412b) respectively in the closure (411) and in the base (410). The closure (411) has a protruding portion (413) which extends into the well (42) of the carrier block (41) when the closure (411) is secured to the base (410). The forward edge (413a) of protrusion (413) is brought into contact with the flange root (44a), while a bevelled side edge (413b) engages O-ring (45). A recess (414) within protrusion (413) defines a sample space in the well (42) above the sensor (40). Inlet and outlet bores (415, 416) formed in the body of the closure (411) allow a carrier fluid to be passed into the sample space to bring test materials into contact with the sensor (40).

As in FIG. 2, the upper surface of the recess (414) is inclined, typically at ca. 2°, to the plane of the sensor (40), and the outlet (416) is positioned at the highest point of the recess (414).

In the embodiment shown, the inlet and outlet bores (415, 416) are inclined to the central axis of the closure (411) to increase the separation of the ports on the upper surface of the closure (411). This gives space for positioning of known HPLC connector bushes in the bores (415, 416). This allows HPLC tubing to be used to flow the carrier liquid in to and out of the cell.

In an alternative embodiment (not shown), for example for situations where the analytical requirements are simply to detect a binding event between a substrate deposited on the sensor surface and a test material suspended or dissolved in the carrier liquid, it is not necessary for the closure part (411) to be provided with inlet and outlet ports and connectors for attaching feed tubing. In this alternative embodiment, the closure (411) is provided with a single port, which may be simply a centrally located aperture or bore hole, through which a carrier liquid can be injected into the well (42) to cover the sensor (40).

Figure 4A:
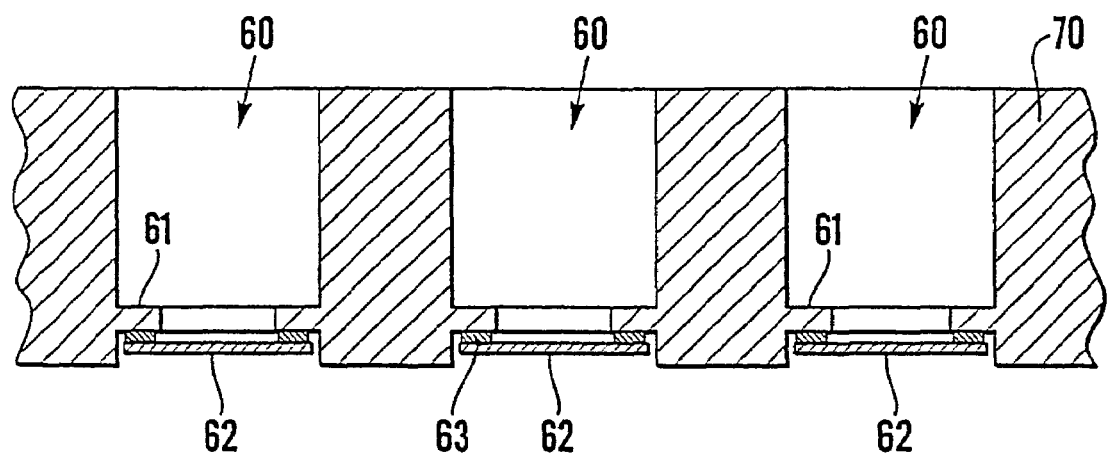
FIGS. 4(a) and (b) are respectively partial sectional and plan views of a multiple static cell unit.
Figure 4B:
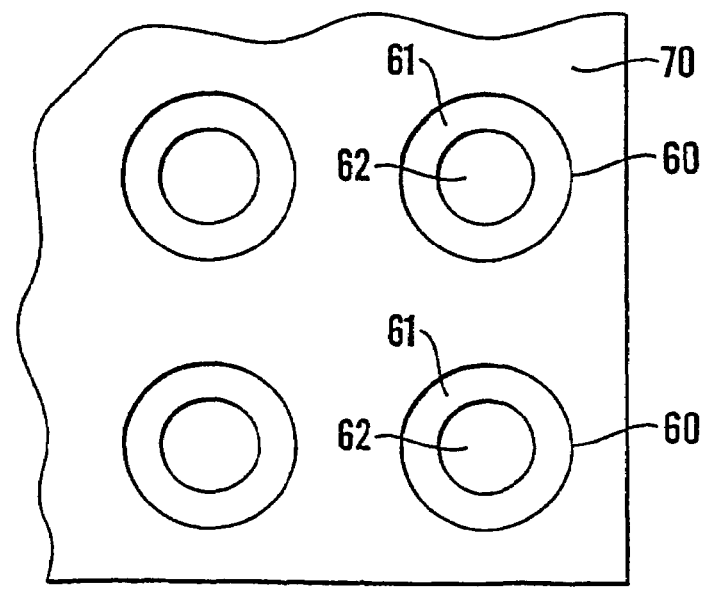

Further, when the quartz crystal sensor cell is not a flow cell, it can be greatly simplified. For example, the cell can be an open well or preferably an array of open wells as shown in FIGS. 4a and 4b. In the embodiment of FIG. 4, a series of wells (60) are formed in a base block (70) in a regular array, suitably 12×8. Each well (60) has an inwardly directed flange towards one end. The well is closed by adhering a quartz crystal sensor (62) to each flange (61) using an adhesive which provides a resilient interlayer (63). The base of the block (70) is provided with electrical connections to power each crystal individually and detect the "Q" output. The base block (70) is suitably dimensioned to be used with existing automated sample injector apparatus whereby a carrier liquid and samples are injected into each well (60), so that binding events may be detected and analysed rapidly and economically on multiple samples.

It is desirable to control the temperature of the samples being tested, in both flow and static testing. An advantage of locating the sensor on the underside of the peripheral flange at the base of each well is that the sensor can be positioned against a Peltier element for temperature control.

A typical quartz crystal sensor (24, 40) is a circular component of diameter of about 8.6 mm. For optimum sensitivity the sample space above the crystal sensor is designed to be as small as possible and in a flow cell a suitable volume is around 20 micro liters. The inlets and outlets are designed to allow the desired flow volume, typically 1 to 100 micro liters per minute. The body parts may be machined or moulded from plastics material preferably a biocompatible polymer such as polyethylethylketone (PEEK) which is non-adherent to proteins, because many applications for quartz crystal microbalances of this type involve assaying binding properties between biological compounds.

When the sensor is secured to a separate carrier (41), then the carrier is also suitably formed from PEEK, allowing the base block (410) to be formed from metal, such as anodised aluminium. In that case the conductive pins (48) are mounted in non-conductive bushes (55).

In a typical use for the cells described above, the quartz crystal sensor (24, 40) is coated with one element of a coupling combination (e.g. a first chemical or biological compound), a sample known or believed to contain the other component of the coupling combination (e.g. a second chemical or biological compound) is passed through the cell using an aqueous carrier, the quartz crystal is driven by an oscillator circuit, and changes in mass of the deposit on the sensor are determined by the frequency change and/or the "Q" value of the driven crystal. These changes may be used to interpret the coupling activity of the compounds under test.

The invention claimed is:

1. A quartz crystal sensor cell comprising a housing, a well in said housing for receiving a sample carrier fluid, said well having a surrounding side and a base with an aperture, said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, in which the base of the well comprises a peripheral flange extending inwardly from said surrounding side of the well, said flange defining said aperture, and in which the adhesive layer forms a resilient interlayer between the sensor and the flange.

2. A cell as claimed in claim 1, in which the well is in the form of a cylindrical bore in said housing, in which said flange is annular in shape and said aperture is circular, and in which the sensor is circular in shape and has a diameter greater than the diameter of said aperture defined by the flange.

3. A cell as claimed in claim 1, in which said well is in the form of a cylinder having said base at one end thereof and being open at an end opposite said one end.

4. A cell comprising a housing, a well in said housing for receiving a sample carrier fluid, said well having a surrounding side and a base with an aperture, said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, and including a closure extending across said well at a location spaced from said sensor.

5. A cell as claimed in claim 4, in which said closure has inlet and outlet ports enabling a fluid sample carrier to pass through the cell.

6. A cell as claimed in claim 4, in which said closure has an aperture allowing a sample carrier fluid to be injected into the well to contact the sensor.

7. A quartz crystal sensor cell comprising a housing, a well in said housing for receiving a sample carrier fluid, said well having a surrounding side and a base with an aperture said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, in which said housing comprises lower and upper housing parts, said lower housing part having said well and said base, in which said aperture is a central aperture in said base, in which the crystal sensor forms at least a part of a first boundary surface of a sample space within said housing, and said upper housing part is located on the lower part, over said well, and in spaced relation to said crystal sensor, said upper housing part forming an upper boundary surface of said sample space.

8. A cell as claimed in claim 7, in which the aperture in said base is defined by a flange having upper and lower sides, said crystal sensor is adhered to the lower side of said flange, a resilient O-ring is seated against the upper side of said flange, said upper housing part is secured to said lower part, and said O-ring is clamped between said upper housing part and the upper side of the flange.

9. A cell as claimed in claim 7, in which the lower housing part comprises a base block and a carrier block, said aperture is formed in said carrier block, said crystal sensor is mounted on said carrier block, said carrier block is received in said base block, and said upper housing part is bolted to the base block and forms a closure for said well.

10. A quartz crystal sensor cell comprising a housing, a well in said housing for receiving a sample carrier fluid, said well having a surrounding side and a base with an aperture, said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, in which said housing has an internal sample space defined in part by a surrounding side wall surface, and an upper housing surface forming an upper end boundary of said sample space, said quartz crystal sensor has a planar face forming at least a part of a lower end boundary of said sample space, and in which said upper housing surface is inclined relative to said planar face of the quartz crystal sensor.

11. A quartz crystal sensor cell according to claim 10, in which said upper housing surface is inclined relative to said planar face of the quartz crystal sensor at an angle in the range from about 10° to 50°.

12. A quartz crystal sensor cell according to claim 10, in which said upper housing surface is inclined relative to said planar face of the quartz crystal at an angle of 2+/−0.5°.

13. A method of use of a quartz crystal sensor cell comprising a housing, a well in said housing for receiving a sample carrier fluid, said well having a surrounding side and a base with an aperture, said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, wherein the quartz crystal sensor is coated with one element of a coupling combination, a sample known or believed to contain the other component of the coupling combination is passed through the cell in an aqueous carrier, the quartz crystal sensor is driven by an oscillator circuit, and changes in mass of the deposit on the sensor are determined by at least one of the frequency change and the "Q" value of the driven crystal.

14. A quartz crystal sensor cell comprising a housing having an internal sample space defined in part by a surrounding side wall surface, a quartz crystal mounted in the housing said quartz crystal having a planar face forming at least a part of a lower end boundary of said sample space, an upper housing surface forming an upper end boundary of said sample space, said housing having inlet and outlet ports for conveying a sample carrier into and out of said sample space, wherein said upper housing surface is inclined relative to said planar face of the quartz crystal sensor.

15. A quartz crystal sensor cell according to claim 14, in which said upper housing surface is inclined relative to said planar face of the quartz crystal sensor at an angle in the range from about 1° to 50°.

16. A quartz crystal sensor cell according to claim 14, in which said upper housing surface is inclined relative to said planar face of the quartz crystal sensor at an angle of 2+/−0.5°.

17. A method of use of a quartz crystal sensor cell according to claim 14, wherein the quartz crystal sensor is coated with one element of a coupling combination, a sample known or believed to contain the other component of the coupling combination is passed through the cell in an aqueous carrier, the quartz crystal sensor is driven by an oscillator circuit, and changes in mass of the deposit on the sensor are determined by at least one of the frequency change and the "Q" value of the driven crystal.

18. A quartz crystal sensor cell comprising a housing (20, 21, 41, 410, 411) having a well (22, 42) to receive a sample carrier fluid, an aperture (23, 43) in the base of the well (22, 43) to receive a quartz crystal sensor (25, 40), and a sensor (25, 40) located in the base of the well (22, 43) so that a peripheral surface of the sensor (25, 40) lies against a peripheral surface of the aperture (23, 43), and the sensor (25, 40) is secured to the base of the well (22, 42) by a layer of adhesive (26) between the respective peripheral surfaces, in which said layer of adhesive (26) forms a resilient interlayer between said respective peripheral surfaces.

19. A quartz crystal sensor cell comprising a housing, a well in said housing for receiving a sample carrier fluid, said well having a surrounding side and a base with an aperture, said aperture having a peripheral surface, a quartz crystal sensor having a peripheral surface overlapping the peripheral surface of the aperture, and a layer of adhesive between the respective peripheral surfaces, securing said peripheral surfaces to each other and thereby securing the quartz crystal sensor to the base, in which said layer of adhesive forms a resilient interlayer between said respective peripheral surfaces.

* * * * *

UNITED STATES PATENT AND TRADEMARK OFFICE
CERTIFICATE OF CORRECTION

PATENT NO.       : 7,055,377 B2
APPLICATION NO.  : 10/344022
DATED            : June 6, 2006
INVENTOR(S)      : Frank Paul et al.

It is certified that error appears in the above-identified patent and that said Letters Patent is hereby corrected as shown below:

Col. 8, claim 11, line 14, "10° to 50°" should read --1° to 5°--;

Col. 8, claim 15, line 48, "50°" should read --5°--.

Signed and Sealed this

Nineteenth Day of September, 2006

JON W. DUDAS
*Director of the United States Patent and Trademark Office*